(12) United States Patent
Fischer et al.

(10) Patent No.: US 12,082,979 B2
(45) Date of Patent: *Sep. 10, 2024

(54) SURGICAL HEAD CLAMP AND ROBOTICS PLATFORM

(71) Applicant: Worcester Polytechnic Institute, Worcester, MA (US)

(72) Inventors: Gregory S. Fischer, Boston, MA (US); Benjamin Piecuch, Mansfield, MA (US); Dino Kasvikis, Mansfield, MA (US); Perry A. Genova, Chapel Hill, NC (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/499,600

(22) Filed: Oct. 12, 2021

(65) Prior Publication Data

US 2022/0031420 A1    Feb. 3, 2022

Related U.S. Application Data

(63) Continuation of application No. 16/253,891, filed on Jan. 22, 2019, now abandoned, which is a
(Continued)

(51) Int. Cl.
*A61B 90/14* (2016.01)
*A61B 17/00* (2006.01)
(Continued)

(52) U.S. Cl.
CPC .............. *A61B 90/14* (2016.02); *A61B 34/20* (2016.02); *A61B 34/25* (2016.02);
(Continued)

(58) Field of Classification Search
CPC ......... A61B 34/20; A61B 34/25; A61B 34/30; A61B 50/13; A61B 90/14; A61B 90/37; A61B 90/50; A61B 2017/00199
See application file for complete search history.

(56) References Cited

U.S. PATENT DOCUMENTS 5,184,601 A    2/1993  Putman
5,254,079 A    10/1993 Agbodoe et al.
(Continued)

OTHER PUBLICATIONS

Piecuch, Benjamin; Issue Notification for U.S. Appl. No. 15/495,767, filed Apr. 24, 2017, mailed Jan. 1, 2019, 1 pg. Note: Copy not required as part of PTO records.
(Continued)

*Primary Examiner* — Jocelin C Tanner
(74) *Attorney, Agent, or Firm* — Taylor English Duma LLP

(57) ABSTRACT

A surgical head clamp and robotics platform secures a head of a patient and positions an instrument relative to the head for a medical procedure. The head clamp and robotics platform comprises a planar C-shaped frame for at least partially encircling the head of a patient. An instrument arm is mounted is to a free distal end of one arm member of the frame. The instrument arm extends away from the arm member in a direction transverse to the plane of the frame. The instrument arm includes a base mounted to the arm member for movement along three degrees of freedom relative to the frame, a proximal portion extending from and pivotally connected to the base, and a distal instrument holder extending from and pivotally connected to the proximal portion. The instrument arm functions to selectively position the instrument in an angular position relative to the head clamp.

4 Claims, 18 Drawing Sheets

Related U.S. Application Data continuation of application No. 15/495,767, filed on Apr. 24, 2017, now Pat. No. 10,182,879.

(60) Provisional application No. 62/364,457, filed on Jul. 20, 2016, provisional application No. 62/326,167, filed on Apr. 22, 2016.

(51) Int. Cl.
*A61B 34/00* (2016.01)
*A61B 34/20* (2016.01)
*A61B 34/30* (2016.01)
*A61B 50/13* (2016.01)
*A61B 90/00* (2016.01)
*A61B 90/50* (2016.01)

(52) U.S. Cl.
CPC ..... *A61B 2017/00199* (2013.01); *A61B 34/30* (2016.02); *A61B 50/13* (2016.02); *A61B 90/37* (2016.02); *A61B 90/50* (2016.02)

(56) References Cited

U.S. PATENT DOCUMENTS

| | | | |
|---|---|---|---|
| 5,269,034 A | 12/1993 | Day et al. | |
| 5,441,042 A | 8/1995 | Putman | |
| 5,537,704 A | 7/1996 | Dinkler | |
| 6,306,146 B1 * | 10/2001 | Dinkler | A61B 90/11 600/417 |
| 6,355,048 B1 * | 3/2002 | Hong | A61B 90/50 606/107 |
| 6,381,783 B2 | 5/2002 | Reinhardt et al. | |
| 6,629,982 B2 | 10/2003 | Day et al. | |
| 7,117,551 B1 * | 10/2006 | Dinkler | A61B 90/14 5/643 |
| 7,229,451 B2 | 6/2007 | Day et al. | |
| 7,507,244 B2 | 3/2009 | Dinkler | |
| 7,661,162 B2 | 2/2010 | Soerensen et al. | |
| 9,204,818 B2 | 12/2015 | Moffatt | |
| 9,254,177 B2 | 2/2016 | Stratton et al. | |
| 10,182,879 B2 * | 1/2019 | Piecuch | A61B 34/20 |
| 2009/0306662 A1 * | 12/2009 | Dinkler | A61B 90/14 606/59 |
| 2012/0323239 A1 * | 12/2012 | Solomon | A61B 17/6433 606/59 |
| 2013/0324834 A1 | 12/2013 | Majewski et al. | |
| 2014/0336647 A1 | 11/2014 | Solomon et al. | |
| 2015/0327937 A1 | 11/2015 | Schuele | |
| 2017/0325906 A1 | 11/2017 | Piecuch et al. | |
| 2019/0223972 A1 | 7/2019 | Fischer et al. | |

OTHER PUBLICATIONS

Piecuch, Benjamin; Notice of Allowance for U.S. Appl. No. 15/495,767, filed Apr. 24, 2017, mailed Sep. 24, 2018, 10 pgs. Note: Copy not required as part of PTO records.

Fischer, Gregory S.; Final Office Action for U.S. Appl. No. 16/253,891, filed Jan. 22, 2019, mailed Jan. 12, 2021, 11 pgs. Note: Copy not required as part of PTO records.

Fischer, Gregory S.; Non-Final Office Action for U.S. Appl. No. 16/253,891, filed Jan. 22, 2019, mailed Sep. 16, 2020, 13 pgs. Note: Copy not required as part of PTO records.

* cited by examiner

SURGICAL HEAD CLAMP AND ROBOTICS PLATFORM

CROSS-REFERENCES

This application is a continuation of U.S. patent application Ser. No. 16/253,891, filed Jan. 22, 2019, which is a continuation of U.S. patent application Ser. No. 15/495,767, filed Apr. 24, 2017, now U.S. Pat. No. 10,182,879, which claims the benefit of U.S. Provisional Application Ser. No. 62/326,167, filed Apr. 22, 2016, and U.S. Provisional Application Ser. No. 62/364,457, filed Jul. 20, 2016, the entire disclosures of which are hereby incorporated by reference in their entirety.

BACKGROUND

A surgical head clamp is described for securing a head of a patient in position for neurosurgical operations and other procedures and, more particularly, a surgical head clamp and robotics platform suitable for positioning an instrument for use in both magnetic resonance imaging (MRI) of the head and stereotactic neurosurgical procedures.

Surgical head clamps, sometimes referred to as skull clamps, are useful in holding a head of a patient during neurosurgical procedures during which the head must be completely immobilized due to the extremely delicate nature of the procedures. A conventional head clamp comprises a pair of articulating arms forming a C-shaped frame member for partially encircling the head of a patient. Movable pins are provided at each end of the frame member for engaging and securing the head of the patient at a plurality of points. The two arms are brought together to adjust the space between the engaging pins to fit the dimensions of the head of the patient. The pins are configured to penetrate the flesh and engage the outer layer of bone of the skull. Adjustment knobs may be provided for translating the pins axially thereby adjusting the distance between the pins to facilitate securing the head. Once attached to the patient, the head clamp can be mounted to an operating table or other support structure, thereby immobilizing the head of the patient during the surgical procedure.

In stereotactic neurosurgery, a neurosurgeon will often have to insert instruments, such as electrodes or catheters, into the brain with extreme accuracy. In particular, the success of stereotactic neurosurgery is highly dependent on the accuracy with which the neurosurgical instruments can be guided to a predetermined target site within the brain. Magnetic resonance imaging (MRI) is often used to plan the surgery and guide positioning of the instruments. With MRI, a high field magnet is arranged in a torus configuration with the patient lying on a table inside the magnet. However, conventional head clamps may hamper access to a head location for the surgeon and interference with preferred hand or instrument positions or may further limit the use of MRI.

For the foregoing reasons, there is a need for a surgical head clamp for use in neurosurgical and other procedures for accurately accessing with instruments predetermined target sites within the brain of the patient. Ideally, the surgical head clamp will be configured for use with MRI for guiding the instruments to the target sites.

SUMMARY

A surgical head clamp and robotics platform is provided for securing a head of a patient and positioning an instrument relative to the head of the patient for a medical procedure. The head clamp and robotics platform comprises a planar C-shaped frame for at least partially encircling the head of a patient. The frame includes a first arm member and a second arm member. The second arm member is connected at one end to an end of the first arm member in a telescoping relationship for selectively adjusting the distance between the free ends of the first and second arm members. A mounting bracket is at each of the free ends of the first arm member and the second arm member. The brackets extend away from the first and second arm members in a direction transverse to the plane of the frame. Each bracket defines an opening, and a pin for engaging the head of the patient and movably received in each of the openings of the brackets. The pins are adapted to adjustably extend toward the head of the patient for securing the head of the patient in the head clamp.

In one aspect, an instrument arm is mounted to a free distal end of one of the first arm member or the second arm member. The instrument arm extends away from the one of the first arm member or the second arm member in a direction transverse to the plane of the frame. The instrument arm includes a base mounted to the one of the first arm member or the second arm member for movement along three degrees of freedom relative to the frame, a proximal portion extending from and pivotally connected to the base for rotation relative to the base, and a distal instrument holder extending from and pivotally connected to the proximal portion for rotation relative to the proximal portion. The instrument arm functions to selectively position the instrument in an angular position relative to the head clamp.

In another aspect, an instrument arm is mounted to a free distal end of one of the first arm member or the second arm member. The instrument arm extends away from the one of the first arm member or the second arm member in a direction transverse to the plane of the frame. The instrument arm includes a base mounted to the one of the first arm member or the second arm member for 360° movement relative to the frame, a proximal portion extending from and pivotally connected to the base for rotation relative to the base, an intermediate portion extending from and pivotally connected to the proximal portion for rotation relative to the proximal portion, and a distal instrument holder extending from and pivotally connected to the intermediate portion for rotation relative to the intermediate portion. The instrument arm functions to selectively position the instrument in an angular position relative to the head clamp.

In yet another aspect, an instrument arm is mounted to a free distal end of one of the first arm member or the second arm member. The instrument arm extends away from the one of the first arm member or the second arm member in a direction transverse to the plane of the frame. The instrument arm includes a base mounted to the one of the first arm member or the second arm member for movement along three degrees of freedom relative to the frame, an elongated arcuate instrument holder, and a motor interconnected between the base and the instrument holder, the motor configured for rotating the instrument holder about an axis passing through the motor and for axially translating the instrument holder such that the instrument holder is positioned relative to the base between the proximal end of the instrument holder and the distal end of the instrument holder. The instrument arm functions to selectively position the instrument in an angular position relative to the head clamp.

In a further aspect, an instrument arm is mounted to the frame and extends away from the frame in a direction transverse to the plane of the frame. The instrument arm includes a base mounted to a free distal end of one of the first arm member or the second arm member for movement along three degrees of freedom, an elongated arcuate track extending between the free distal ends of the first arm member and the second arm member, the track configured for rotation about an axis passing through the ends of the track, and an instrument holder mounted to the track for axially translating along the track between the ends of the first and second arm members. The instrument arm functions to selectively position the instrument in an angular position relative to the head clamp.

BRIEF DESCRIPTION OF THE DRAWINGS

For a more complete understanding of the surgical head clamp and robotics platform, reference should now be had to the embodiments shown in the accompanying drawings and described below. In the drawings.

DESCRIPTION

Figure 1:
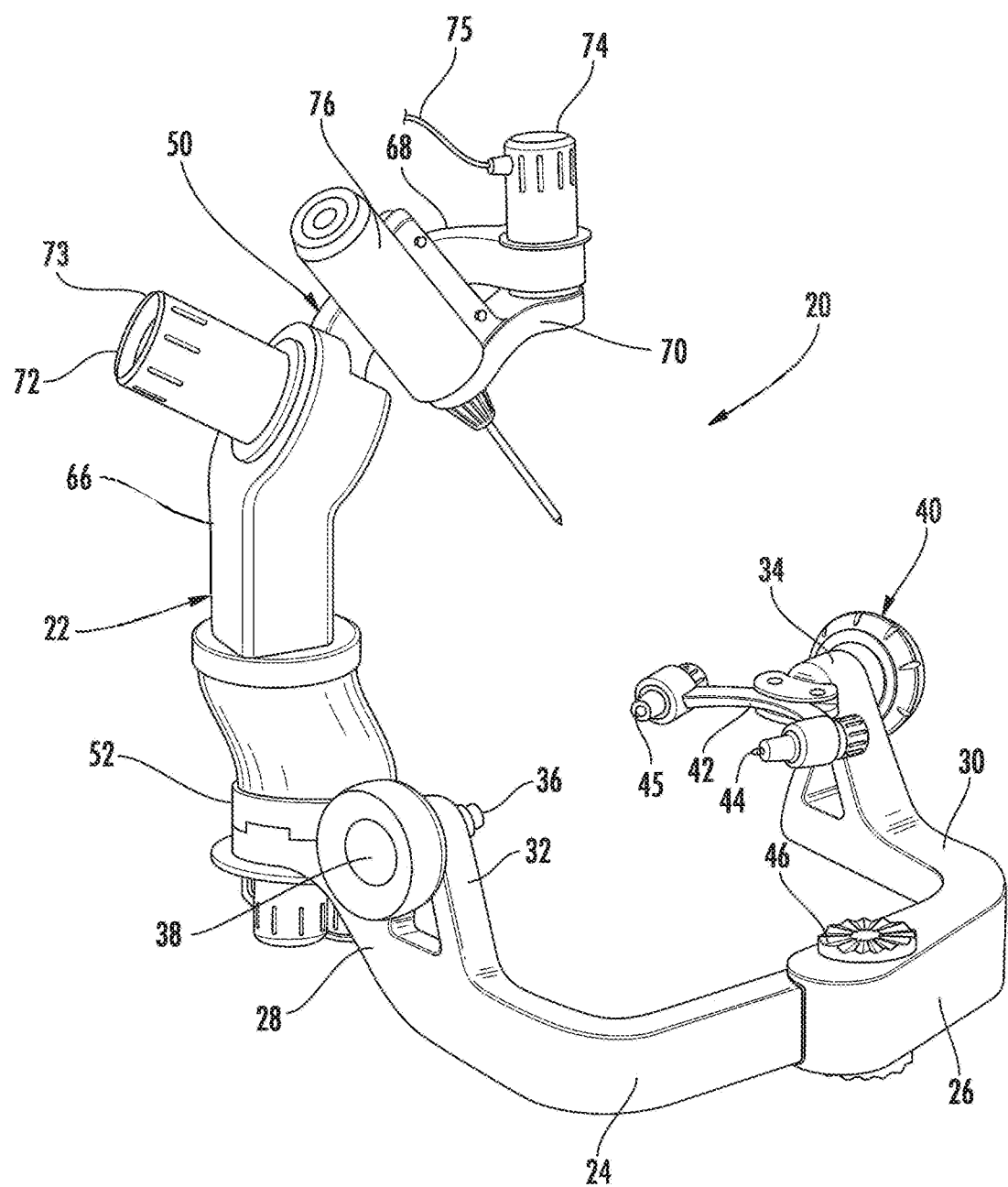
FIG. 1 is a perspective view of an embodiment of a surgical head clamp and robotics platform.

Referring now to the drawings, wherein like reference numbers indicate same or similar elements throughout the several views, there is shown in FIG. 1 an embodiment of a surgical head clamp generally designated at 20. The head clamp 20 includes an integral robotics platform 22 adjustably connected to the head clamp 20. The head clamp 20 provides a structure capable of immobilizing the head of a patient for medical procedures. The robotics platform 22 provides means for penetrating bone of the skull of the patient at a precise location for accessing the brain.

The surgical head clamp 20 comprises a generally C-shaped frame including a first frame member 24 and a second frame member 26. The first and second frame members 24, 26 are connected in a telescoping relationship with the first frame member 24 being capable of telescoping into, or out of, the second frame member 26. The frame members 24, 26 each have arms 28, 30 extending forwardly from the connection. Each of the arms 28, 30 includes a pin mounting bracket 30, 32 extending away from the frame member 24, 26 in a direction transverse to the plane of the head clamp 20. The bracket 32 on the arm 28 of the first frame member 24 defines an internally threaded bore for threadably receiving a head engaging pin 36. The pin 36 has an integral knob 38 at a proximal end. A dual pin holding means 40 is mounted to the bracket 34 at the distal end of the opposite arm 30. The pin holding means 40 includes a V-shaped carriage 42 mounted in the bracket 34 for rotation relative to the bracket about an axis perpendicular to the plane of the V-shaped carriage 42. The V-shaped carriage 42 receives at its ends a second head engaging pin 44 and a third head engaging pin 45. Selective rotation of the V-shaped carriage 42 about its axis permits the surgeon to adjust the angular relationship between the frame member 26 and the patient's head so that the pins 44, 45 on the V-shaped carriage 42 can accommodate varying geometries of the head.

The pins 36, 44, 45 on the C-shaped frame are in suitable orientations so as to engage the head from opposite sides. The pins 36, 44, 45 extend inwardly from the brackets 32, 34 toward the head of a patient for securing the head in the head clamp 20 by and between the three head engaging pins 36, 44, 45, respectively, which are pressed into the head on opposite sides thereof. The distal ends of the pins 36, 44, 45 terminate in sharpened tips adapted to penetrate the flesh and soft tissue covering the skull and to slightly penetrate the outer layer of bone of the skull in order to provide an anchor needed to secure the head.

The head clamp 20 includes independently hand driven mechanisms for application of pressure to support the head. A hand-operated wheel 46 is mounted in the proximal end of the second frame member 26 to size or position the head clamp 20 with respect to a patient's head. The wheel 46 is provided for adjusting the width between the distal ends of the arms 28, 30 by relative telescoping movement of the frame members 24, 26. As the wheel rotates, the width of the C-shaped frame at the distal ends of the arms 28, 30 is adjusted. This coarse adjustment thus allows movement of one arm relative to the other arm to a position near the head where the pins 36, 44, 45 are brought into engagement with the head to apply pressure through the pins to the skull. Fine adjustment by the knobs 38 tightens the pins 36, 44, 45.

The head clamp 20 may be secured to the operating room table or other supporting structure through a support (not shown) which would be affixed to the table so as to hold the clamp underneath the head and thus to support the head in an adjusted fixed position relative to the table. This provides a selected fixed configuration relative to the clamp 20 and the table to provide a rigid and immovable head clamp system for the duration of the surgical procedure being conducted.

The robotics platform 22 includes a curved instrument arm 50 mounted to the distal end of the arm 28 of the frame member 24. The instrument arm 50 features an angular positioning mechanism for releasably positioning an instrument in a selected angular position and relative to the head clamp 20. The instrument arm 50 comprises a base 66, a proximal portion 68 extending from the base and a distal instrument holder 70.

Figure 2:
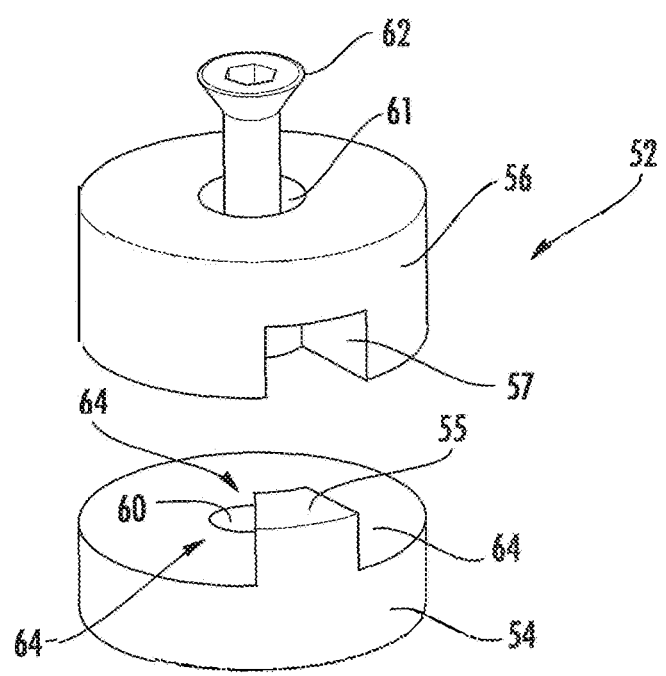
FIG. 2 is an exploded perspective view of a locking mount for mounting the robotics platform to the surgical head clamp as shown in FIG. 1.
Figure 3:
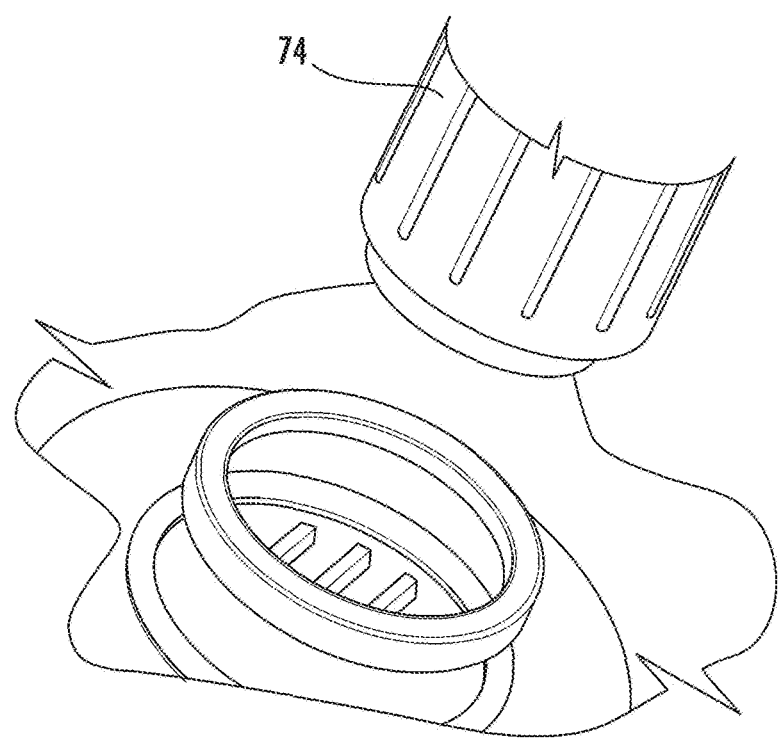
FIG. 3 is a partial exploded perspective view of a sterile connection for use with the surgical head clamp and robotics platform as shown in FIG. 1.

An embodiment of a mount 52 for interconnecting the bead clamp 20 and the instrument arm 50 is shown in FIG. 2 and includes a pair of interlocking discs 54, 56. The bottom disc 54, as seen in FIG. 2, is integral with the distal end of the arm 28, and the top disc 56, as seen in FIG. 2, is integral with the base 66 of the instrument arm 50. The bottom disc 54 has an axially extending protrusion 55 extending from an inner surface. The top disc 54 has a radially extending slot 57 configured for receiving the protrusion 55 such that the discs 54, 56 rotate together. The discs 54, 56 each define a central axial opening 60, 61 for receiving a threaded fastener 62 for securing the instrument arm 50 to the head clamp 20. A plurality of fiducials 64 are provided on the inner surface of each disc 54, 56 for aligning the discs. The instrument arm 50 is releasably attachable to the head clamp 20 via the mount 52 in a repeatable position relative to the head clamp. A motor pack is operatively connected to the base 66 for movement of the base along three degrees of freedom (XYZ table) for adjustably positioning the instrument arm 50.

The instrument arm 50 is offset from the plane of the head clamp 20. This relative configuration of the head clamp 20 and the instrument arm 50 removes the instrument arm 50 from interfering with imaging and surgical access of the head. The majority of the mass of the head clamp 20 is located in areas where it will not negatively impact the image orientations of the patient's head thus keeping the head clamp 20 out of the field of images of the skull. The instrument arm 50 is located to the side keeping the mechanism out of the field of images taken from the top or bottom, as well as lateral imaging. The configuration also enables neurosurgical procedures (e.g. stereotactic neurosurgery) to be performed on the head. The surgeon has access, substantially unhindered by the head clamp 20 and robotics platform 22, to the required part of the head through which the brain will be accessed. The relative positions of the head clamp 20 and the instrument arm 50 optimize access for neurosurgery.

A proximal end of the proximal portion 68 of the instrument arm 50 is rotatably connected to the distal end of the base 66. A drive motor 72 is positioned at the junction of the base 66 and the first proximal portion 68 for rotating the proximal portion of the instrument arm 50 in a first plane. Similarly, a proximal end of the instrument holder 70 is rotatably connected to the distal end proximal portion 68 of the arm 50. A drive motor 74 is positioned at the junction of the first proximal portion 68 and the instrument holder 70 for rotating the instrument holder in a second plane. Each of the motors 72, 74 drives a rotating drive shaft which is engaged with a proximal end of rotating member. When activated, for example, under the control of a computer-controller system, the motors cause the rotating members to rotate so as to move the instrument 76 to different positions or to a required position. In one embodiment, the motors 72, 74 are electric motors; however, any other suitable drive system, such as pneumatic or hydraulic, would also a powered or motorized drive.

The components of the head clamp 20 and robotics platform 22 may be made from an MRI compatible material, including polyetheretherketone (PEEK), Novotex, or any other non-ferromagnetic material that can be placed in a magnetic field and non-electrically conductive so that they do not affect radio frequency fields. Other suitable non-ferromagnetic materials which are compatible with MR and X-ray imaging can be used, such as but not limited to titanium, polymeric, carbon fiber, ceramic, glass-filled polymer or other composite materials, so as to permit the use of the system during an MRI procedure on the patient. It would also be possible to use a ferrous metal (such as steel) if MRI compatibility was not required.

Figure 4:
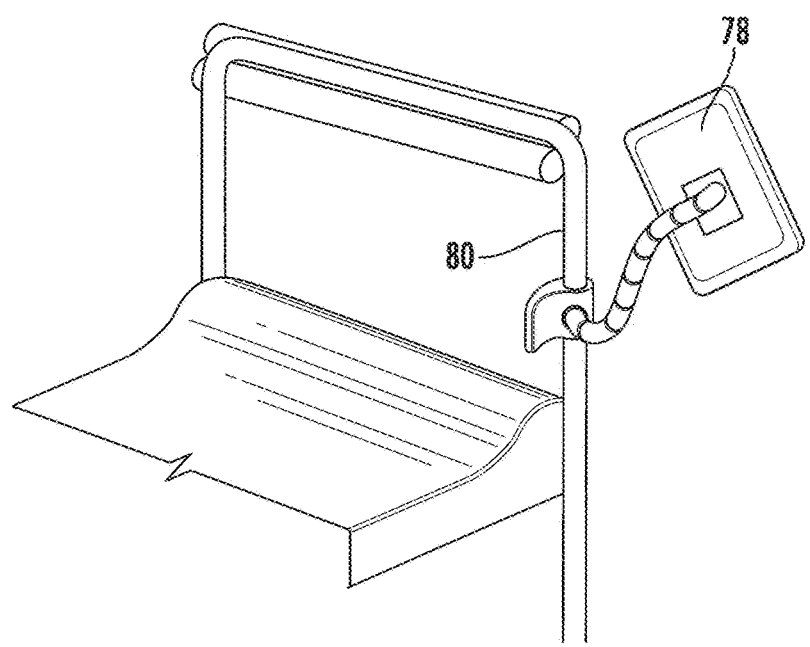
FIG. 4 is a perspective view of a user interface mounted to a bed cart for use with the surgical head clamp and robotics platform shown in FIG. 1.
Figure 5:
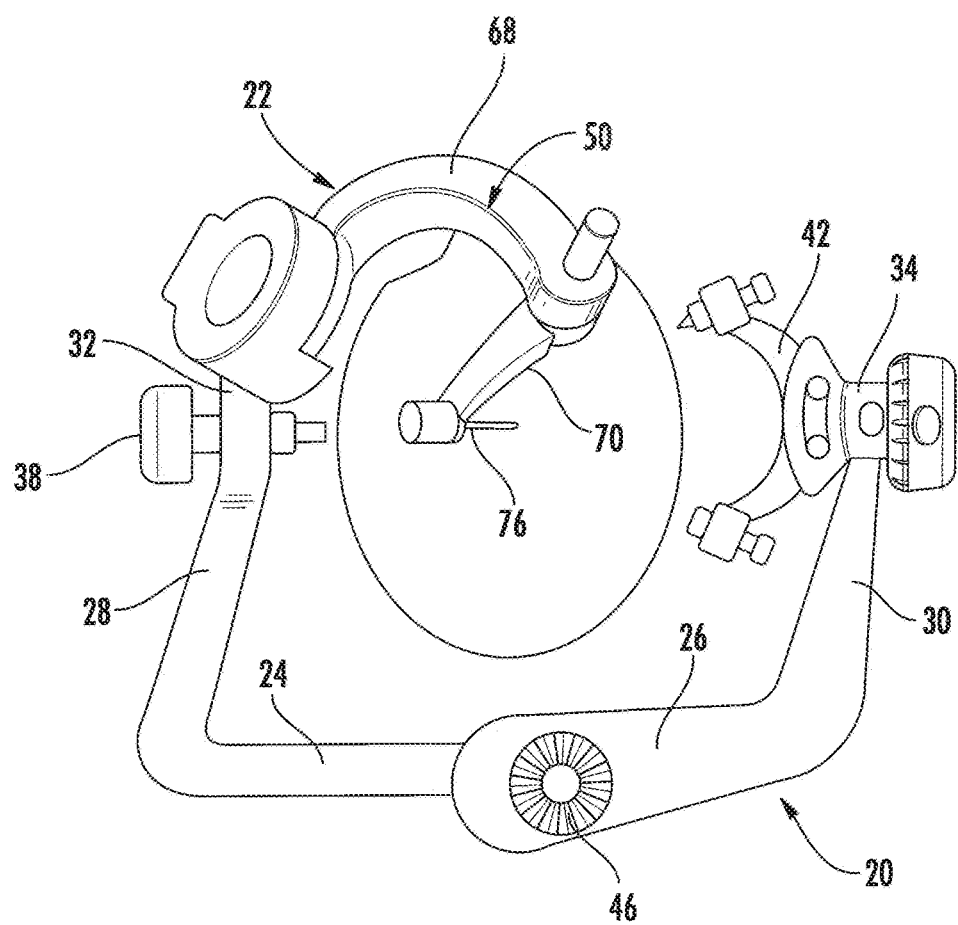
FIG. 5 is a top plan view of the surgical head clamp and robotics platform shown in FIG. 1 in place on a head of a patient.

A positioning mechanism is provided for adjusting the position of the instrument 76 with respect to the head clamp 20. The positioning mechanism comprises the rotatable portions of the instrument arm 50 for allowing the instrument to be oriented as desired. In one embodiment, the rotatable portions of the instrument arm 50 are automatically and selectively driven into position using a powered drive system subject to a computer controller. The computer controller allows a medical professional using the head clamp 20 and robotics platform 22 to predetermine the location of the instrument as desired via a user interface, such as a keypad 78 shown in FIG. 4 mounted to a bed 80. Information can be transmitted by direct wired signal cables or by wireless means including antennas for receipt by a remote monitoring system for observation by any member of the surgical team assisting the surgeon. Signals are relayed via respective signal cables 73, 75 to the motors 72, 74 and back to the controller. The controller also provides electrical power to the drive motors 72, 74 through the cables 73, 75. The digital data of the position of the instrument applied against the skull and in the brain can be displayed on a monitor screen of the interface. Additional mechanical and positional adjustment can be provided by the head clamp 20, as desired.

In use, the frame members 24, 26 of the C-shaped frame are separated and the patient's head is positioned between. In this arrangement, the C-shaped frame extends around and across the head from the first arm 28 to the second arm 30. The frame members 24, 26 are then moved together until the head-engaging pins 36, 44, 45 are in contact with the patient skull. The pins 36, 44, 45 are then moved inwardly into the bony portion of the skull a sufficient distance to hold the skull in the correct position for the surgical procedure. Previously acquired images of the brain can be used, such as MRI images, after applying appropriate coordinate transformations, to precisely guide neurosurgical instruments, even when the head clamp 20 has been moved. In particular, once an MRI image of the head has been obtained, position information acquired from the MRI images can then be prepared relative to the head clamp 20 and be used to precisely target regions or points in the brain. The head clamp 20 may also be indexed, to any further position that is suitable for conducting a surgical procedure. The ability to move the frame members 24, 26 and the instrument arm 50 into a plurality of repeatable relative positions is particularly advantageous.

The surgical head clamp and robotics platform 22 has many advantages applicable to neuro-surgery, wherein the instrument arm 50 is used for retaining and guiding neurosurgical instruments. The neurosurgical instruments guided by the instrument arm 50 attached to the head clamp 20 may be accurately guided to target sites in the brain identified using MRI, even though the head clamp 20 may be indexed into different positions during imaging and surgery. The different positions allow optimized imaging or provide the necessary access to the head for the insertion of neurosurgery devices or instruments.

Figure 6:
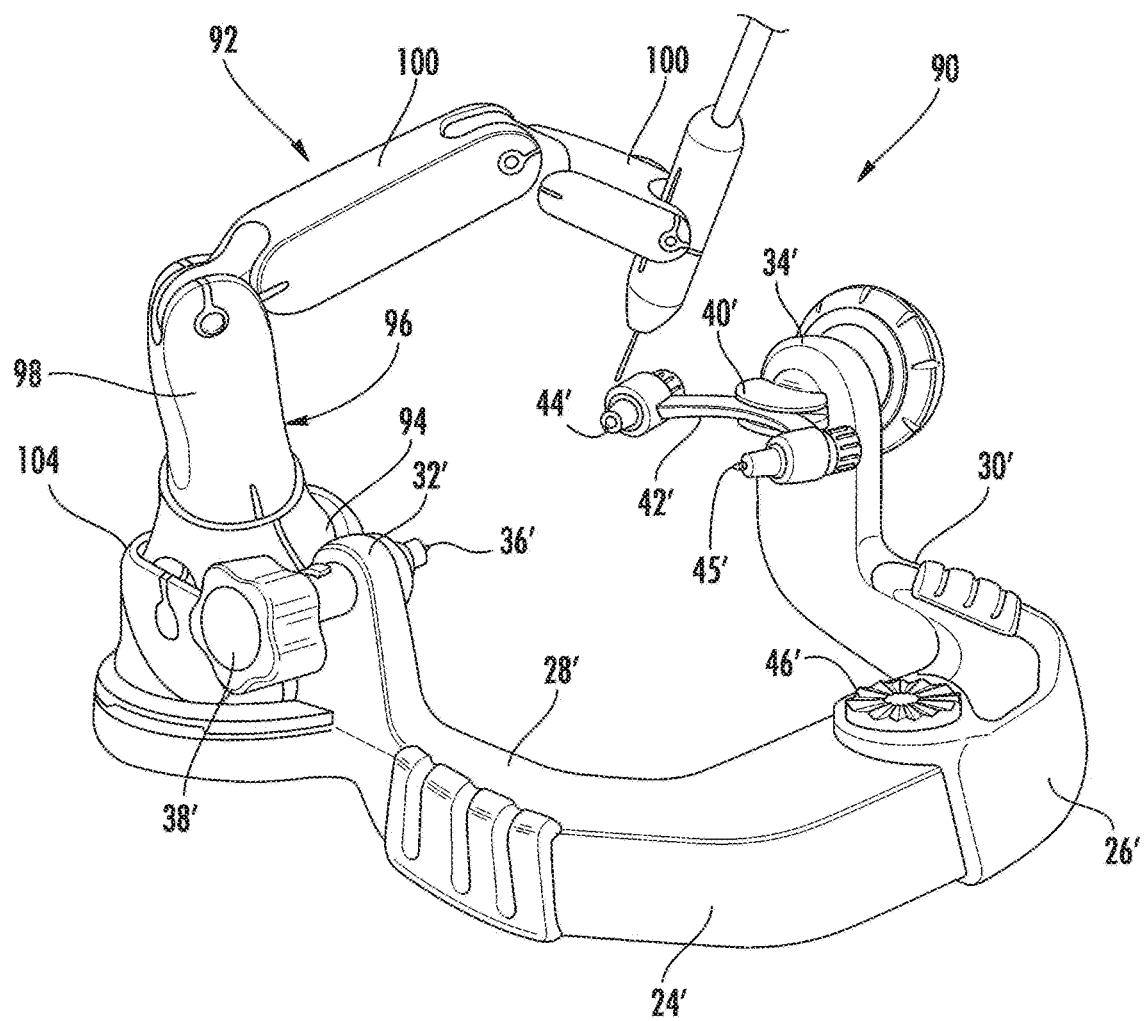
FIG. 6 is a perspective view of a second embodiment of a surgical head clamp and robotics platform.
Figure 7:
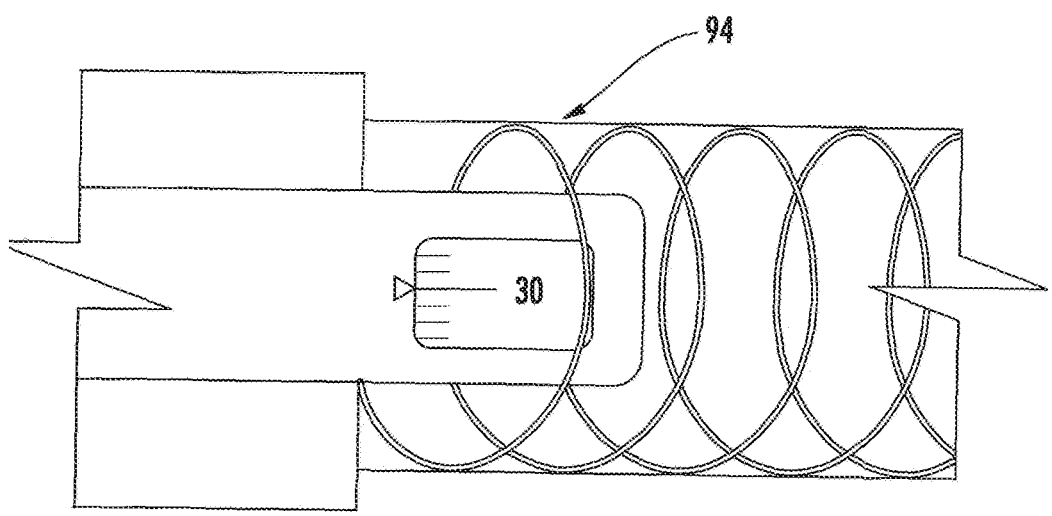
FIG. 7 is an up-close elevation vim of a gauge for measuring force of a spring loaded pin for use with the surgical head clamp shown in FIG. 6.
Figure 8:
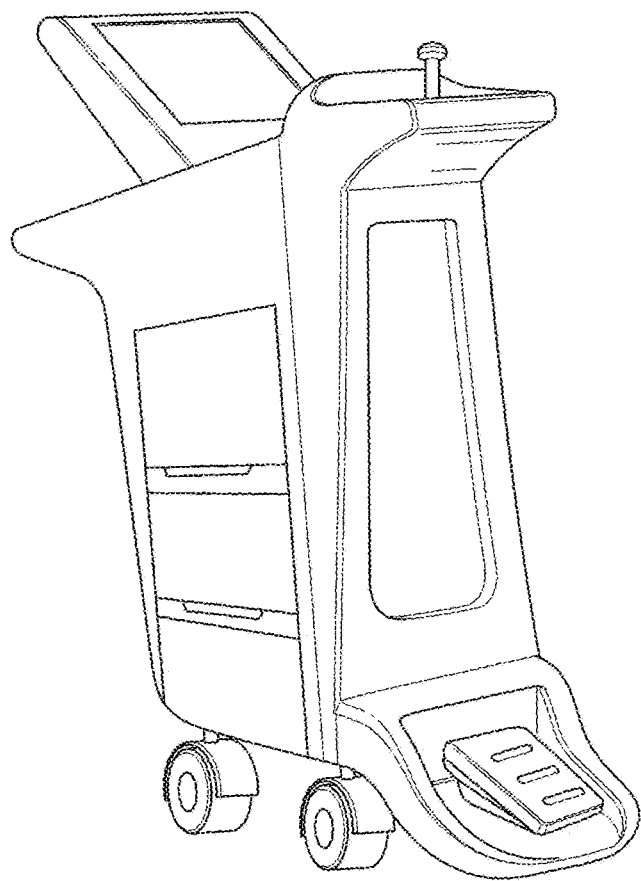
FIG. 8 is a perspective view of a cart for housing the surgical head clamp and robotics platform shown in FIG. 6 and including a user interface.

Referring now to the FIGS. 6-9, wherein like reference numbers designated as prime (') from the first embodiment indicate same or similar elements, there is shown in FIG. 6 another embodiment of a surgical head clamp generally designated at 90. This embodiment of the head clamp 90 includes an integral robotics platform 92 adjustably connected to the head clamp 90. The surgical head clamp 90 comprises a generally C-shaped frame, including a first frame member 24' telescoping into, or out of a second frame member 26'. Pin mounting brackets 32', 34' extend away from the ends of the frame members 24', 26' in a direction transverse to the plane of the head clamp 90 for mounting head engaging pins 36', 44' 45'. The pins 36', 44', 45' extend inwardly from the brackets 32', 34' toward the head of a patient for securing the head in the head clamp 90. A hand-operated wheel 46' provides coarse adjustment to position the pins 36', 44', 45' into engagement with the head to apply pressure through the pins to the skull. Fine adjustment by knobs 38' tightens the pins 36', 44', 45'. The force of the first pin 36' against the skull may be measured by a pin force indicator 94 integral with the first knob 38' (FIG. 7).

The robotics platform 92 includes a multi-joint instrument arm 96 mounted to the distal end of the arm 28' of the first frame member 24'. The instrument arm 96 features an angular positioning mechanism for releasably positioning an instrument in a selected angular position relative to the head clamp 90. The instrument arm 96 comprises a base 98 and an intermediate arm 100 interconnecting the base 98 and a distal instrument holder 102. The base 98 includes a ball-and-socket joint wherein the socket is defined by a mount 104 for interconnecting the head clamp 90 and the instrument arm 96. The proximal end of the base 98 forms a ball-shape and is received in the corresponding socket of the mount 104. The base 98 has full 360 degree rotational and pivoting movement relative to the mount 104. The distal end of the base 98 is pivotally connected to the proximal end of the intermediate arm 100 for rotation about an axis. The intermediate arm is movable relative to the base 98 in a plane perpendicular to the axis of rotation of the intermediate arm 100 and the base 96. The distal end of the intermediate arm 100 is pivotally connected to the proximal end of the instrument holder 102 for rotation about an axis. The instrument holder 102 is movable relative to the intermediate arm 100 in a plane perpendicular to the axis of rotation of the intermediate arm 100 and the instrument holder 102. As in the previous embodiment, the instrument arm 96 is offset from the plane of the head clamp 90 for minimizing interference with imaging and surgical access to the head.

A drive motor (not shown) engages the proximal end of the base 98 of the instrument arm 96 for rotating the base 98 relative to the mount 104. When activated, for example, under the control of a computer-controller system, the motor causes the base 98 to rotate in the socket of the mount 204 so as to move the instrument arm 96 to different positions or to a required position. In one embodiment, the motor is an electric motor; however, any other suitable drive system, such as pneumatic or hydraulic, would also a powered or motorized drive.

Figure 9:
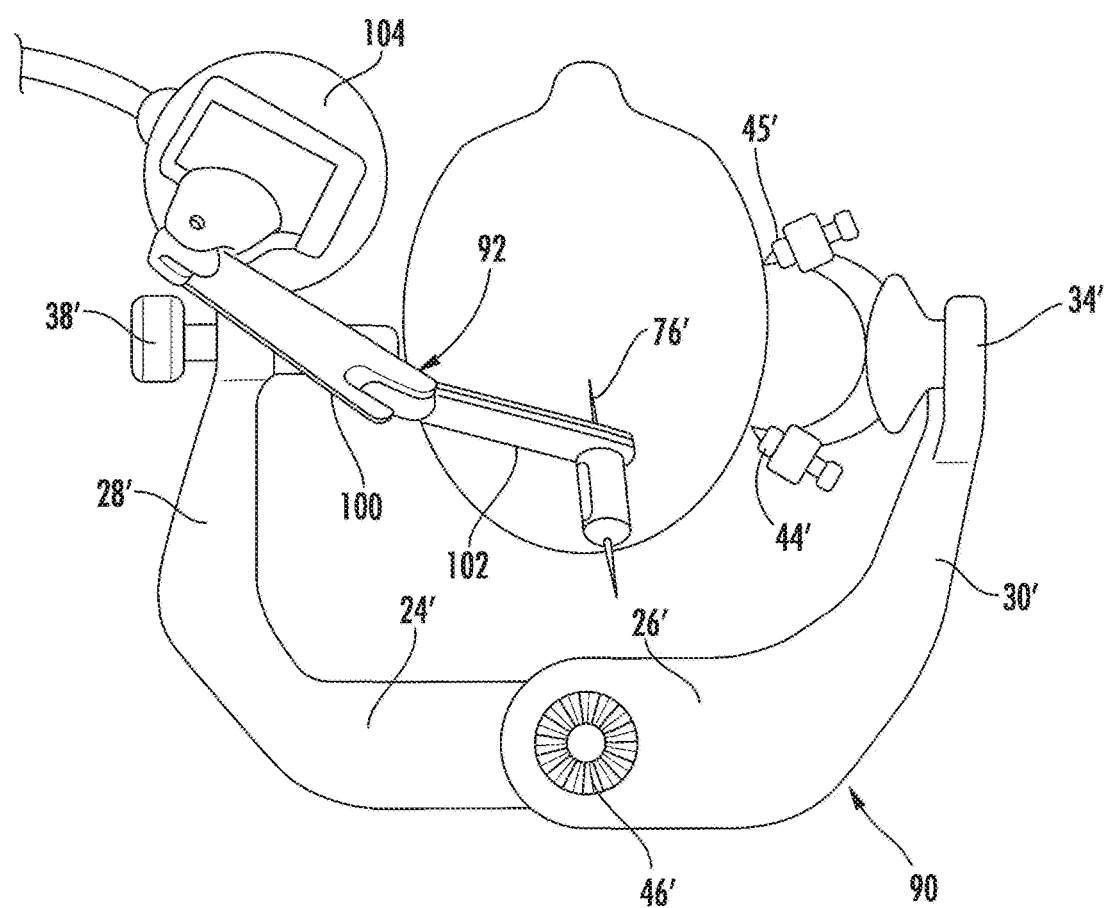
FIG. 9 is a top plan view of the surgical head clamp and robotics platform shown in FIG. 6 in place on a head of a patient.

As shown in FIG. 9, the head clamp 90 provides a structure capable of immobilizing the head of a patient for medical procedures. The robotics platform 92 provides means for penetrating bone of the skull of the patient at a precise location for accessing the brain as described above with respect to the first embodiment.

Figure 10:
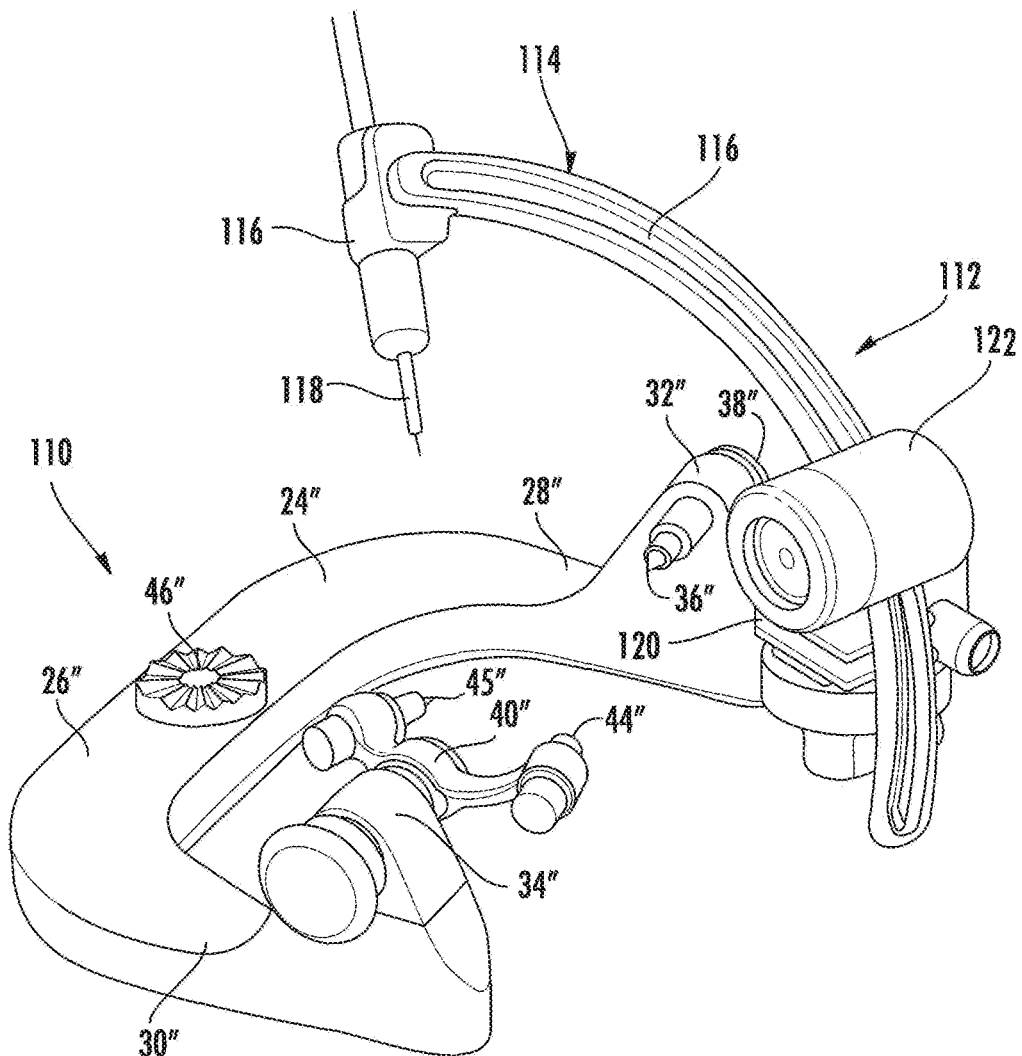
FIG. 10 is a perspective view of a third embodiment of a surgical head clamp and robotics platform.
Figure 11:
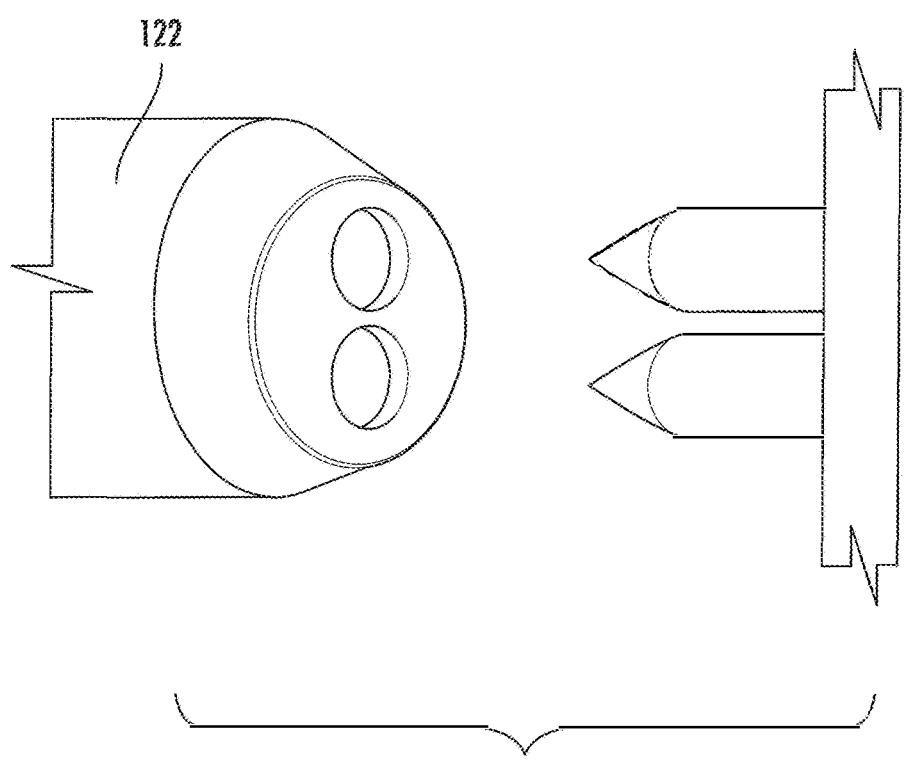
FIG. 11 is a partial exploded perspective view of a sterile connection for use with the surgical head clamp and robotics platform as shown in FIG. 10.
Figure 12:
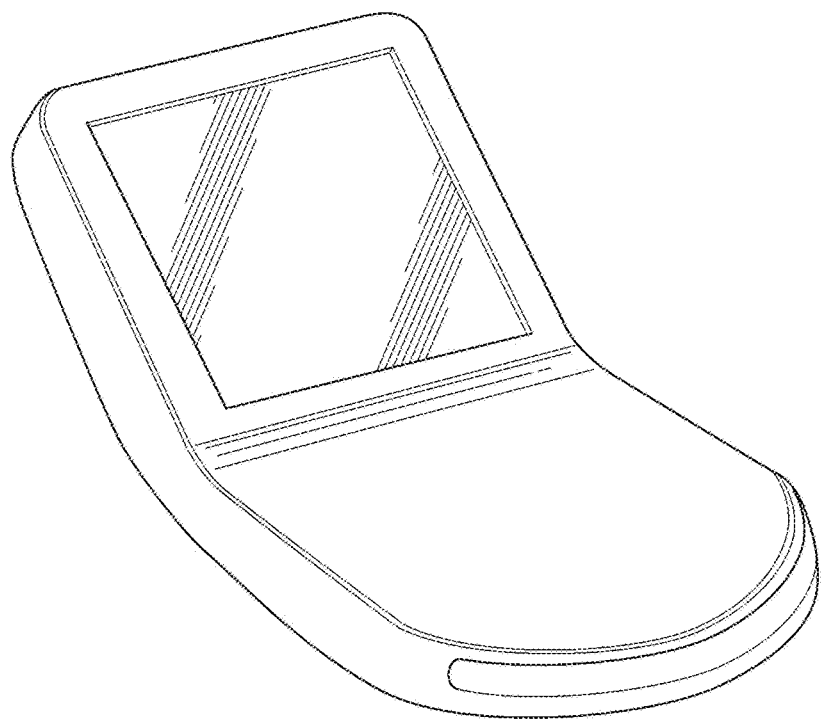
FIG. 12 is a perspective view of a user interface including joystick control for use with the surgical head clamp and robotics platform as shown in FIG. 10.

Referring now to the FIGS. 10-13, wherein like reference numbers designated as double prime (") from the first and second embodiments indicate same or similar elements, there is shown in FIG. 10 a third embodiment of a surgical head clamp generally designated at 110. This embodiment of the head clamp 110 includes an integral robotics platform 112 adjustably connected to the head clamp 110. The surgical head clamp 110 comprises a generally C-shaped frame, including a first frame member 24" pivotally connected at one end to a second frame member 26". Pin mounting brackets 32", 34" extend away from the ends of the frame members 24", 26" in a direction transverse to the plane of the head clamp 110 for mounting head engaging, pins 36", 44" 45". The pins 36", 44", 45" extend inwardly from the brackets 32", 34" toward the head of a patient for securing the head in the head clamp 90. Relative pivoting of the first and second frame members 24", 26" allows movement of the pins 36", 44", 46" toward and away from the head of the patient. A hand-operated wheel 46" provides further coarse adjustment of the pins 36", 44", 45" into engagement with the head to apply pressure through the pins to the skull. Fine adjustment by knobs 38" tightens the pins 36", 44", 45".

The robotics platform 112 includes an arcuate instrument arm 114 mounted to the distal end of the first frame member 24". The instrument arm 114 defines a longitudinal slot 115 extending for substantially the length of the instrument arm 114. An instrument holder 116 is disposed at the distal end of the instrument arm 114. The instrument arm 114 features an angular positioning mechanism for positioning an instrument 118 in a selected angular position relative to the head clamp 110. An XYZ table 120 interconnects the head clamp 110 and the instrument arm 114. A drive motor is provided for translating the instrument arm 114 along any of the three axes of the XYZ table 120. A second drive motor 122 is provided for engaging and advancing the instrument arm 114 in both directions along the slot 115 for movement of the instrument arm 114 along a curvilinear path relative to the XYZ table. In one embodiment, the motor is an electric motor; however, any other suitable drive system, such as pneumatic or hydraulic, would also a powered or motorized drive. The instrument arm 114 may be also be rotated about an axis passing though the motor 122. When activated, for example, under the control of a computer-controller system, the motors cause the instrument arm 114 to move to different positions or to a required position relative to the head clamp 110. As in the previous two embodiments, the instrument arm 114 is offset from the plane of the head clamp 110 for minimizing interference with imaging and surgical access to the head.

Figure 13:
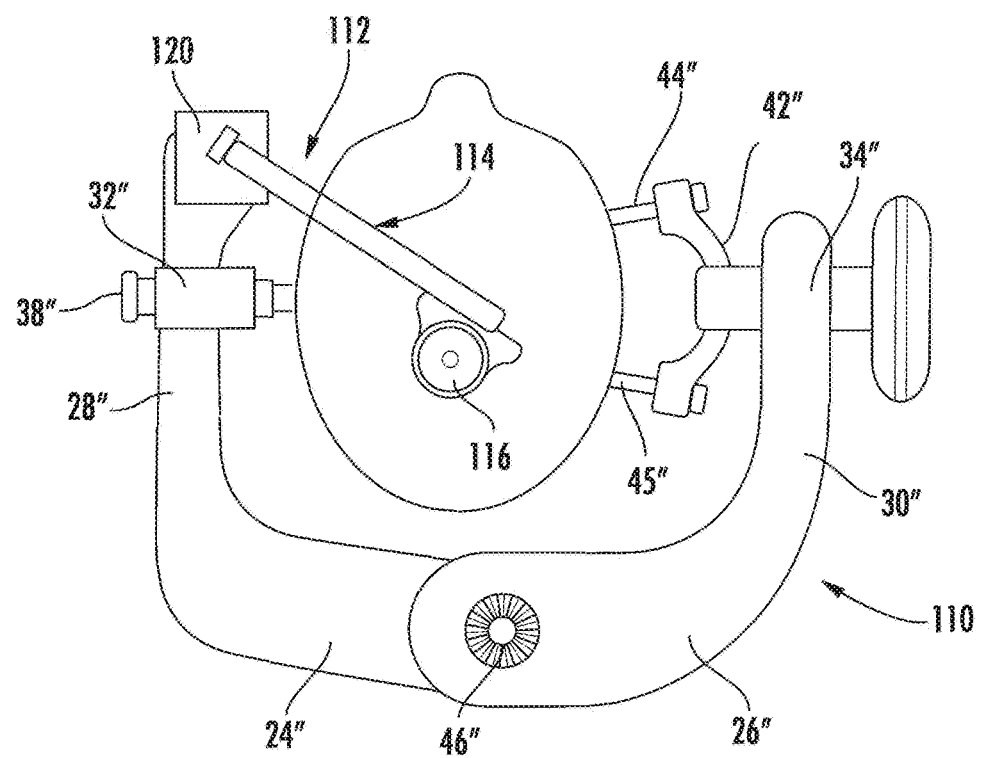
FIG. 13 is a top plan view of the surgical head clamp and robotics platform shown in FIG. 10 in place on a head of a patient.

As shown in FIG. 13, the head clamp 11 provides a structure capable of immobilizing the head of a patient for medical procedures. The robotics platform 112 provides means for penetrating bone of the skull of the patient at a precise location for accessing the brain as described above with respect to the first embodiment.

Figure 14:
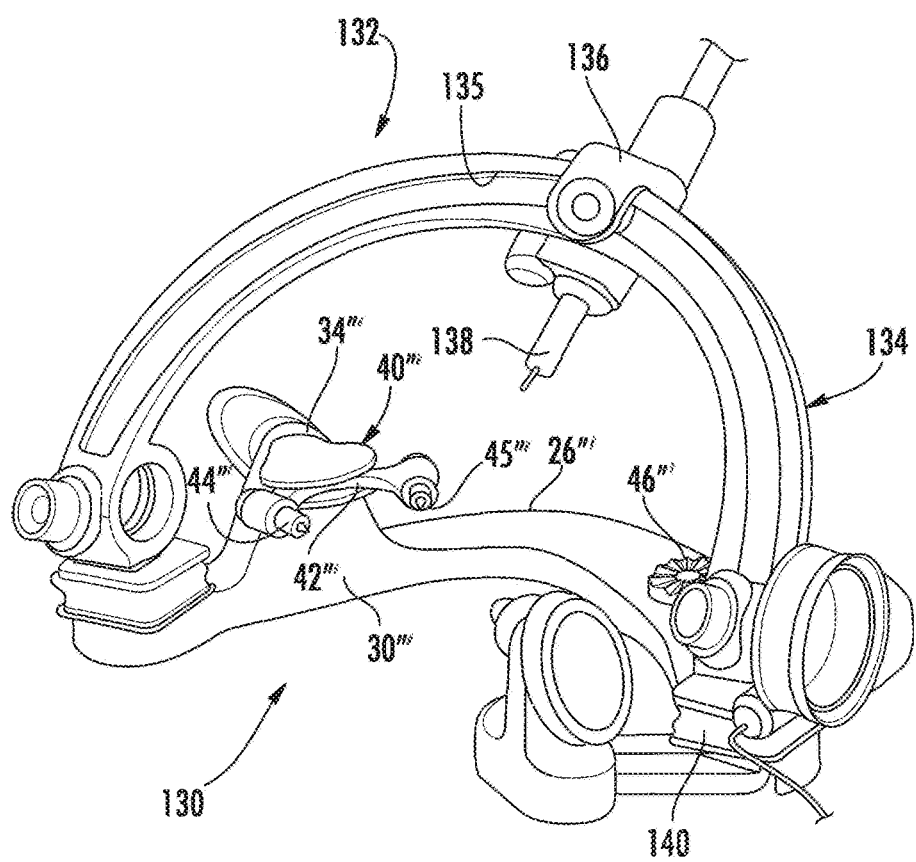
FIG. 14 is a perspective view of a fourth embodiment of a surgical head clamp and robotics platform.
Figure 15:
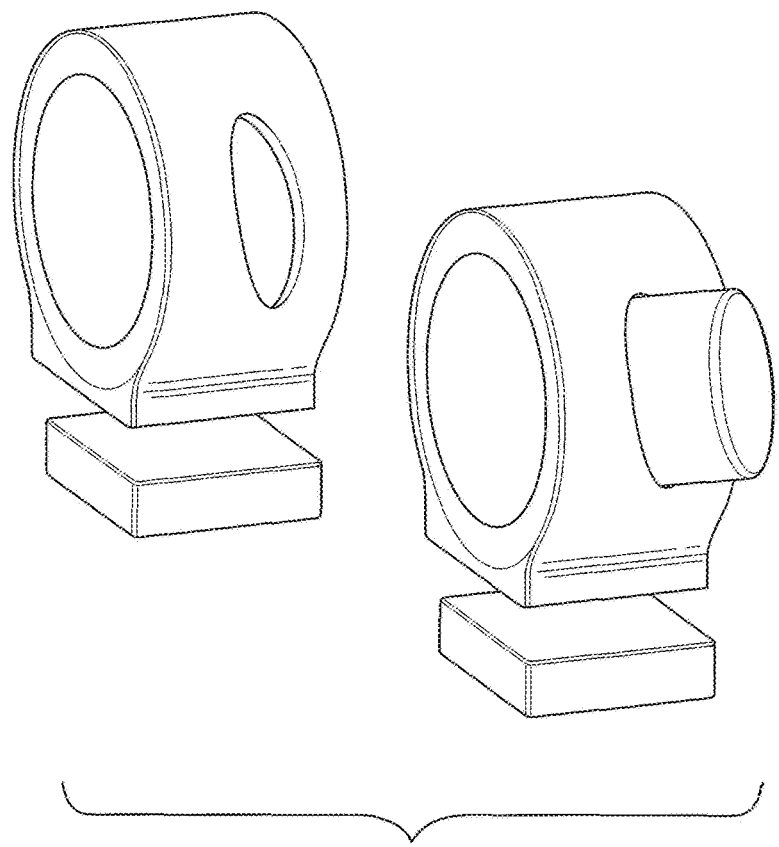
FIG. 15 is a partial perspective view of a locking mount for mounting the robotics platform to the surgical head clamp as shown in FIG. 14 showing an engaged position and a non-engaged position.
Figure 16:
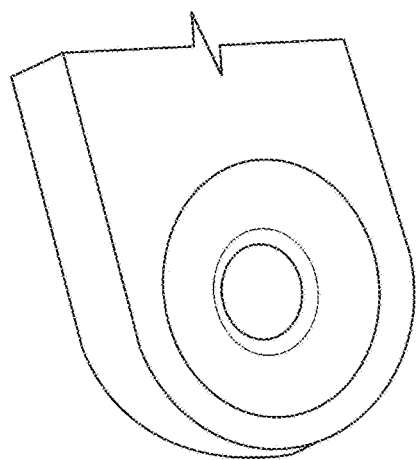
FIG. 16 is partial perspective view of an alarm for use with the surgical head clamp and robotics platform as shown in FIG. 14.
Figure 17:
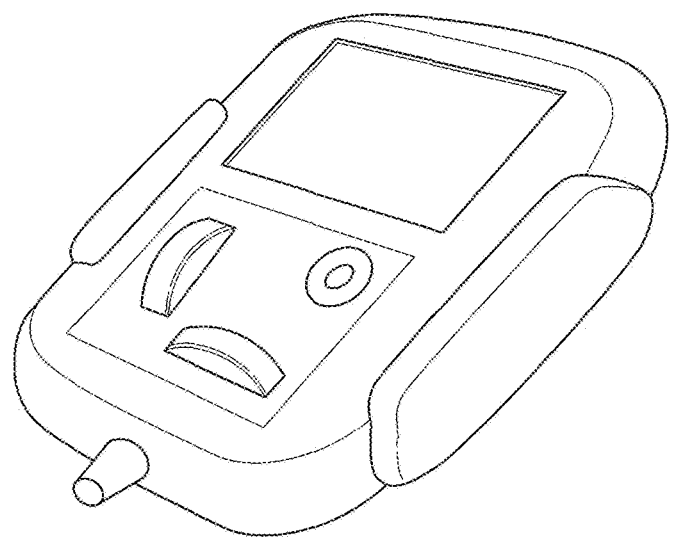
FIG. 17 is a perspective view of a hand-held user interface for use with the surgical head clamp and robotics platform as shown in FIG. 14.

Referring now to the FIGS. 14-18, wherein like reference numbers designated as triple prime ('") from the first, second and third embodiments indicate same or similar elements, there is shown in FIG. 14 a fourth embodiment of a surgical head clamp generally designated at 130. This embodiment of the head clamp 130 includes an integral robotics platform 132 adjustably connected to the head clamp 130. The surgical head clamp 130 comprises a generally C-shaped frame, including a first frame member 24''' pivotally connected at one end to a second frame member 26'''. Pin mounting brackets 32''', 34''' extend away from the ends of the frame members 24''', 26''' in a direction transverse to the plane of the head clamp 130 for mounting head engaging pins 36''', 44''' 45'''. The pins 36''', 44''', 45''' extend inwardly from the brackets 32''', 34''' toward the head of a patient for securing the head in the head clamp 130. Relative pivoting of the first and second frame members 24''', 26''' allows movement of the pins 36''', 44''', 46''' toward and away from the head of the patient. A hand-operated wheel 46''' provides further coarse adjustment of the pins 36''', 44''', 45''' into engagement with the head to apply pressure through the pins to the skull. Fine adjustment by knobs 38''' tightens the pins 36''', 44''', 45'''.

The robotics platform 132 includes an arcuate instrument arm 134 pivotally mounted between the distal ends of the frame members 24''', 26'''. The instrument arm 134 defines a longitudinal slot 135 extending for substantially the length of the instrument arm 134. An instrument holder 136 is slidably disposed in the slot 135 of the instrument arm 134. The instrument holder 136 is movable in the slot 135 for advancing the instrument holder in both directions along a curvilinear path relative to the head clamp 130. The instrument arm 134 features an angular positioning mechanism for positioning an instrument 138 in a selected angular position relative to the head clamp 130. An XYZ table 140 interconnects the head clamp 130 and the instrument arm 134. A drive motor 142 is provided for translating the instrument arm 134 along any of the three axes of the XYZ table 140. In one embodiment, the motor is an electric motor; however, any other suitable drive system, such as pneumatic or hydraulic, would also a powered or motorized drive. The instrument arm 134 may be also be rotated about an axis passing though the distal ends of the frame members 24''', 26'''. When activated, for example, under the control of a computer-controller system, the motor causes the instrument arm 134 to move to different positions or to a required position relative to the head clamp 130. As in the previous three embodiments, the instrument arm 134 is offset from the plane of the head clamp 130 for minimizing interference with imaging and surgical access to the head.

Figure 18:
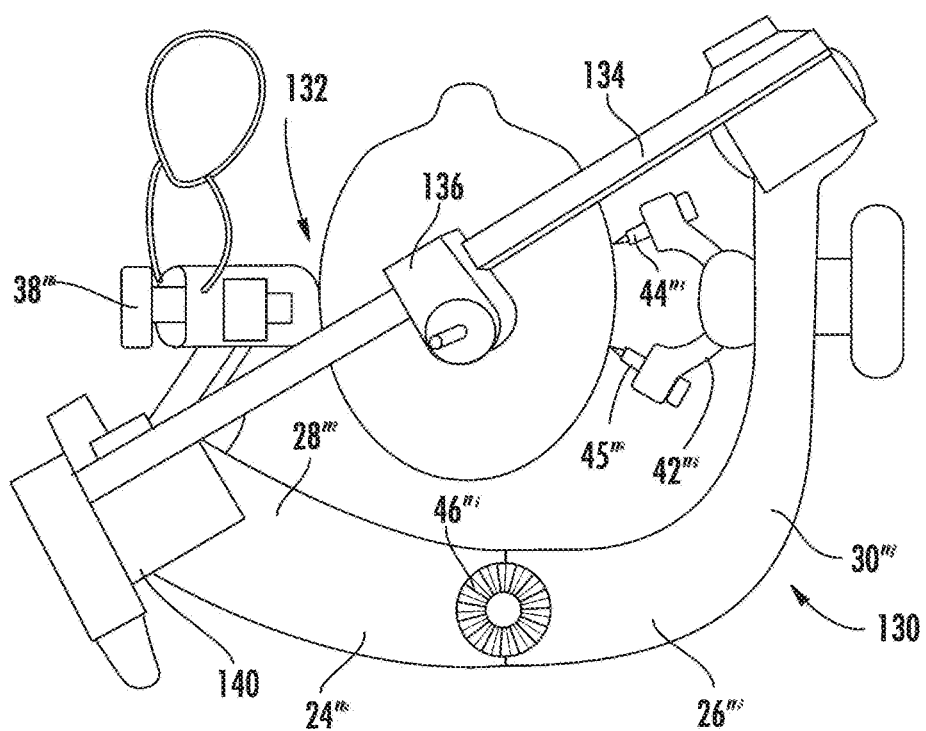
FIG. 18 is a top plan view of the surgical head clamp and robotics platform shown in FIG. 14 in place on a head of a patient.

As shown in FIG. 18, the head clamp 130 provides a structure capable of immobilizing the head of a patient for medical procedures. The robotics platform 132 provides means for penetrating bone of the skull of the patient at a precise location for accessing the brain as described above with respect to the first embodiment.

Although the present invention has been shown and described in considerable detail with respect to only a few exemplary embodiments thereof, it should be understood by those skilled in the art that we do not intend to limit the surgical head clamp and robotics platform to the embodiments since various modifications, omissions and additions may be made to the disclosed embodiments without materially departing from the novel teachings and advantages, particularly in light of the foregoing teachings. Accordingly, we intend to cover all such modifications, omission, additions and equivalents as may be included within the spirit and scope of the surgical head clamp and robotics platform as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. A surgical head clamp and robotics platform for securing a head of a patient and positioning an instrument relative to the head of the patient for a medical procedure, the head clamp and robotics platform comprising:

a planar C-shaped frame for at least partially encircling the head of a patient, the frame including
  a first arm member having a connecting end and a free end,
  a second arm member having a connecting end and a free end, the second arm member connected at the connecting end to the connecting end of the first arm member in a telescoping relationship for selectively adjusting the distance between the free ends of the first and second arm members,
  a mounting bracket at each of the free ends of the first arm member and the second arm member, the brackets extending away from the first and second arm members in a direction transverse to the plane of the frame, each bracket defining an opening, and
  a pin for engaging the head of the patient and movably received in each of the openings of the brackets, the pin adapted to adjustably extend toward the head of the patient for securing the head of the patient in the head clamp;

an instrument arm mounted to a free distal end of one of the first arm member or the second arm member, the instrument arm extending away from the one of the first arm member or the second arm member in a direction transverse to the plane of the frame, the instrument arm including
  a base mounted to the one of the first arm member or the second arm member for movement along three degrees of freedom relative to the frame, a proximal portion extending from and pivotally connected to the base for rotation relative to the base, and
  a distal instrument holder extending from and pivotally connected to the proximal portion for rotation relative to the proximal portion, wherein the instrument arm functions to selectively position the instrument in an angular position relative to the head clamp;

a powered drive system for changing the position of the instrument arm relative to the frame; and a computer controller for controlling the drive system for positioning the instrument arm to a predetermined location.

2. A surgical head clamp and robotics platform for securing a head of a patient and positioning an instrument relative to the head of the patient for a medical procedure, the head clamp and robotics platform comprising:

a planar C-shaped frame for at least partially encircling the head of a patient, the frame including
  a first arm member having a connecting end and a free end,
  a second arm member having a connecting end and a free end, the second arm member connected at the connecting end to the connecting end of the first arm member in a telescoping relationship for selectively adjusting the distance between the free ends of the first and second arm members, a mounting bracket at each of the free ends of the first arm member and the second arm member, the brackets extending, away from the first and second arm members in a direction transverse to the plane of the frame, each bracket defining an opening, and a pin for engaging the head of the patient and movably received in each of the openings of the brackets, the pin adapted to adjustably extend toward the head of the patient for securing the head of the patient in the head clamp; and an instrument arm mounted to a free distal end of one of the first arm member or the second arm member, the instrument arm extending away from the one of the first arm member or the second arm member in a direction transverse to the plane of the frame, the instrument arm including a base mounted to the one of the first arm member or the second arm member for 360° [ ] movement relative to the frame, a proximal portion extending from and pivotally connected to the base for rotation relative to the base, an intermediate portion extending from and pivotally connected to the proximal portion for rotation relative to the proximal portion, and a distal instrument holder extending from and pivotally connected to the intermediate portion for rotation relative to the intermediate portion, wherein the instrument arm functions to selectively position the instrument in an angular position relative to the head clamp;

a powered drive system for changing the position of the instrument arm relative to the frame; and a computer controller for controlling the drive system for positioning the instrument arm to a predetermined location.

3. A surgical head clamp and robotics platform for securing a head of a patient and positioning an instrument relative to the head of the patient for a medical procedure, the head clamp and robotics platform comprising:

a planar C-shaped frame for at least partially encircling the head of a patient, the frame including a first arm member having a connecting end and a free end, a second arm member having a connecting end and a free end, the second arm member connected at the connecting end to the connecting end of the first arm member in a telescoping relationship for selectively adjusting the distance between the free ends of the first and second arm members, a mounting bracket at each of the free ends of the first arm member and the second arm member, the brackets extending away from the first and second arm members in a direction transverse to the plane of the frame, each bracket defining an opening, and a pin for engaging the head of the patient and movably received in each of the openings of the brackets, the pin adapted to adjustably extend toward the head of the patient for securing the head of the patient in the head clamp; and an instrument arm mounted to a free distal end of one of the first arm member or the second arm member, the instrument arm extending away from the one of the first arm member or the second arm member in a direction transverse to the plane of the frame, the instrument arm including a base mounted to the one of the first arm member or the second arm member for movement along three degrees of freedom relative to the frame, an elongated arcuate instrument holder having a proximal end and a distal end, and a motor interconnected between the base and the instrument holder, the motor configured for rotating the instrument holder about an axis passing through the motor and for axially translating the instrument holder such that the instrument holder is positioned relative to the base between the proximal end of the instrument holder and the distal end of the instrument holder, wherein the instrument arm functions to selectively position the instrument in an angular position relative to the head clamp;

a powered drive system for changing the position of the instrument holder relative to the frame; and a computer controller for controlling the drive system for positioning the instrument holder to a predetermined location.

4. A surgical head clamp and robotics platform for securing a head of a patient and positioning an instrument relative to the head of the patient for a medical procedure, the head clamp and robotics platform comprising:

a planar C-shaped frame for at least partially encircling the head of a patient, the frame including a first arm member having a connecting end and a free end, a second arm member having a connecting end and a free end, the second arm member connected at the connecting end to the connecting end of the first arm member in a telescoping relationship for selectively adjusting the distance between the free ends of the first and second arm members, a mounting bracket at each of the free ends of the first arm member and the second arm member, the brackets extending away from the first and second arm members in a direction transverse to the plane of the frame, each bracket defining an opening, and a pin for engaging the head of the patient and movably received in each of the openings of the brackets, the pin adapted to adjustably extend toward the head of the patient for securing the head of the patient in the head clamp; and an instrument arm mounted to the frame and extending away from the frame in a direction transverse to the plane of the frame, the instrument arm including a base mounted to a free distal end of one of the first arm member or the second arm member for movement along three degrees of freedom, an elongated arcuate track extending between the free distal ends of the first arm member and the second arm member, the track configured for rotation about an axis passing through the ends of the track, and an instrument holder mounted to the track for axially translating along the track between the ends of the first and second arm members, wherein the instrument arm functions to selectively position the instrument in an angular position relative to the head clamp;

a powered drive system for changing the position of the instrument holder relative to the frame; and a computer controller for controlling the drive system for positioning the instrument holder to a predetermined location.

* * * * *